United States Patent [19]

Moorehead

[11] 4,388,221
[45] Jun. 14, 1983

[54] VANADIUM-PHOSPHORUS-TIN-MORDENITE OXIDATION CATALYSTS

[75] Inventor: Eric L. Moorehead, Diamond Bar, Calif.

[73] Assignee: Union Oil Company of California, Los Angeles, Calif.

[21] Appl. No.: 289,806

[22] Filed: Aug. 3, 1981

[51] Int. Cl.$^3$ .............................................. B01J 27/14
[52] U.S. Cl. ..................................... 252/435; 252/437
[58] Field of Search ............................... 252/435, 437

[56] References Cited

U.S. PATENT DOCUMENTS

| | | | |
|---|---|---|---|
| 3,862,146 | 1/1975 | Boghosian .................... | 260/346.8 A |
| 3,867,411 | 2/1975 | Raffelson et al. ........... | 260/346.8 A |
| 3,888,886 | 6/1975 | Young et al. ................. | 260/346.8 A |
| 3,915,892 | 10/1975 | Harrison ............................. | 252/435 |
| 3,977,998 | 8/1976 | Freerks et al. ..................... | 252/435 |
| 4,062,873 | 12/1977 | Harrison ......................... | 252/437 X |
| 4,064,070 | 12/1977 | Harrison ......................... | 252/437 X |
| 4,092,269 | 5/1978 | Mount et al. ...................... | 252/435 |
| 4,123,388 | 10/1978 | Kerr et al. ........................ | 252/437 |
| 4,151,116 | 4/1979 | McDermott ....................... | 252/435 |
| 4,153,577 | 5/1979 | Barone ............................... | 252/435 |
| 4,165,299 | 8/1979 | Pederson ........................... | 252/435 |
| 4,165,300 | 8/1979 | Dolhyj et al. ..................... | 252/462 |
| 4,179,404 | 12/1979 | Barone ............................... | 252/435 |
| 4,206,084 | 6/1980 | Strojny et al. ................. | 252/455 R |
| 4,252,680 | 2/1981 | Walker et al. ................. | 252/437 X |

*Primary Examiner*—Delbert E. Gantz
*Assistant Examiner*—William G. Wright
*Attorney, Agent, or Firm*—Dean Sandford; Gregory F. Wirzbicki; Cleveland R. Williams

[57] ABSTRACT

Oxidation catalysts having large surface areas and which are suitable for converting $C_4$ to $C_{10}$ hydrocarbons to maleic anhydride are disclosed, comprising the oxides of vanadium, phosphorus and tin in combination with hydrogen mordenite having a surface area between 100 $M^2/g$ to 450 $M^2/g$ and wherein the vanadium has an average valence in the range of from 3.5 to 4.95.

31 Claims, No Drawings

VANADIUM-PHOSPHORUS-TIN-MORDENITE OXIDATION CATALYSTS

BACKGROUND OF THE INVENTION

1. Field of the Invention

The present invention relates to oxidation catalysts, and more particularly to mordenite oxidation catalysts which are useful for producing maleic anhydride from $C_4$ to $C_{10}$ hydrocarbons.

2. The Prior Art

Essentially all of the catalysts and methods disclosed in the prior art are for producing maleic anhydride from $C_4$ and higher hydrocarbons employ oxidation catalysts containing vanadium in a valence state of less than +5. One method of forming such catalysts is to impregnate a catalyst base with a vanadium compound in which the vanadium has a valence of less than +5. Another more desirable method involves impregnating the catalyst with a vanadium compound which has a vanadium in the +5 valence state and then reducing the vanadium from the +5 valence state to a valence less than +5.

Several references disclose oxidation catalysts containing vanadium-phosphorus mixed oxide catalysts and methods of preparing the same. For example, U.S. Pat. No. 4,179,404 discloses a process for preparing vanadium-phosphorus containing oxidation catalysts which consists of reducing pentavalent vanadium to a valence of less than +5 with a trivalent phosphorus compound. The phosphorus compound is employed in a concentration of from about 75 to 90 percent of the stoichiometric amount necessary to reduce the vanadium to a valency of from +5 to +4.

U.S. Pat. No. 4,153,577 discloses a catalyst complex useful for the partial oxidation of alkanes to the corresponding anhydrides in a vapor phase reaction. The oxidation catalyst used is a reduced vanadium and phosphorus mixed oxide catalyst containing either transition metals, Group IIA metals or rare earth metals.

Another oxidation catalyst suitable for preparing maleic anhydride from normal $C_4$ hydrocarbons is disclosed in U.S. Pat. No. 4,123,388 which relates to a vanadium, phosphorus, copper mixed oxide complex containing an alkali or alkaline earth metal. In addition, tin is described as a desirable metal for incorporating into the catalyst.

U.S. Pat. No. 4,092,269 relates to vanadium-phosphorus oxidation catalysts wherein at least 20 atom percent of the vanadium is in the tetravalent state. A pore modification agent selected from polymeric materials, cellulosic materials, monosaccharides, etc. is added to the catalyst to provide pore diameters between 0.8 to 10 microns. The catalyst is described as useful for the conversion of aliphatic hydrocarbons to maleic anhydride.

Finally, U.S. Pat. No. 3,915,892 discloses a method of preparing a vanadium-phosphorus mixed oxide oxidation catalyst utilizing three bulk phase transitions, wherein the average valence of vanadium is maintained in the range of 4.1 to 4.5 and in addition a partial pressure of oxygen is maintained in contact with the mixed oxides formed.

As can readily be determined from the above, there is an ongoing effort to develop oxidation catalysts for preparing maleic anhydride from alkanes and olefins.

Accordingly, it is an object of the present invention to provide an improved oxidation catalyst for oxidizing saturated and unsaturated hydrocarbons to maleic anhydride.

Another object of the present invention is to provide an oxidation catalyst having a large surface area which is useful for producing maleic anhydride and to provide a method of preparing the same.

A further object of the present invention is to provide a method for obtaining improved yields and selectivity of maleic anhydride and, in addition, improvements in catalyst stability.

These and other objects are accomplished according to the present invention by oxidizing either a saturated or unsaturated hydrocarbon having from four to ten carbon atoms in the presence of an oxidation catalyst comprising the oxides of vanadium, phosphorus, tin on a hydrogen mordenite support.

SUMMARY OF THE INVENTION

The present invention resides in an oxidation catalyst described by the formula:

$$V_aP_bSn_cO_dX$$

wherein X is mordenite, a is from 0.10 to 1, b is 1, c is from 0.001 to 0.30, and d is a number which satisfies the valence requirements of the other elements present.

The invention additionally resides in a method of preparing a vanadium, phosphorus, tin, mixed-oxide, mordenite, oxidation catalyst which comprises:

(A) reacting a vanadium compound and a phosphorus compound in an acidic aqueous solution with a tin compound under reaction conditions which will provide vanadium having an average oxidation state of 3.50 to 4.95 to form a catalyst precursor, (B) reacting the catalyst precursor with a binder, solvent and mordenite to form an impregnated mordenite, and (C) calcining the oxidation catalyst at temperatures in the range of from 400° F., for from ½ hour to 6 hours.

A method for producing maleic anhydride is disclosed which comprises reacting a $C_4$ to $C_{10}$ hydrocarbon feedstock with a gas containing molecular oxygen in the vapor phase, under reaction conditions, and in the presence of an oxidation catalyst described by the formula:

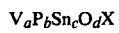
$$V_aP_bSn_cO_dX$$

wherein X is mordenite, a is 0.10 to 1, b is 1, c is 0.001 to 0.30 and d is a number which satisfies the valence requirements of the other elements present.

DETAILED DESCRIPTION OF THE INVENTION

Broadly described, the catalysts of this invention have the general formula:

$$V_aP_bSn_cO_dX$$

wherein X is mordenite, a is from 0.10 to 1, b is 1, and c is from 0.001 to 0.30. The above formula is not an empirical formula, however, the numbers assigned to the subscript letters, i.e., a, b, and c represent the atomic ratio of the respective V, P and Sn active components of the catalyst. The d, in the above formula, may vary widely depending on the mixed oxide combination within the catalyst complex. The only restriction of the d value is that the number assigned to d must satisfy the valency requirements of the other elements in the catalyst complex.

Generally, oxygen combines with the vanadium, phosphorus and tin to form a catalyst precursor which is an oxygen complex or the oxides of these compounds. The oxygen content of the catalyst precursor will vary depending upon the oxidation state of the vanadium, phosphorus and tin utilized. However, d will normally have a value of from 2 to 12, especially from 2 to 8.

The vanadium compounds useful as a source of vanadium in the catalyst precursor are those vanadium compounds known to the art. Suitable vanadium compounds include vanadium salts, such as ammonium metavanadate and vanadyl sulfate; vanadium oxides, such as vanadium pentoxide; and vanadium oxyhalides, such as vanadium oxytrichloride. However, pentavalent vanadium compounds such as ammonium metavanadate and vanadium pentoxide are preferred.

The phosphorus compounds useful as a source of phosphorus in the catalyst precursor are also those known to the art. Suitable phosphorus compounds are selected from phosphoric acid, phosphorus pentoxide, ammonium phosphate and diammonium phosphate. The preferred phosphorus compounds are pentavalent phosphorus compounds such as phosphoric acid and phosphorus pentoxide.

Suitable tin compounds are those tin compounds which have a valence of +2, since the tin compound acts as a reducing agent for the vanadium compound in the catalyst. Tin compounds useful herein preferably are selected from stannous chloride, stannous fluoride, stannous bromide, stannous oxide, stannous sulfate, stannous acetate, stannous pyrophosphate, and stannous oxalate. Upon reaction of the tin compound with the vanadium compound, tin +2 (stannous) will be oxidized up to the tin +4 (stannic) oxidation state and vanadium in the +5 oxidation state will be reduced to an average oxidation state of less than +5.

The catalyst precursor is preferably produced by dissolving and mixing compounds of vanadium, phosphorus and tin in an acidic-aqueous medium such as water and hydrochloric acid, hydroiodic acid, hydroformic acid, acetic acid, oxalic acid, maleic acid, citric acid or formic acid. The vanadium-phosphorus-tin compounds are contacted at an atomic ratio of vanadium-phosphorus-tin of from 0.10:1:0.001 to 1:1:0.30, especially from 0.20:1:0.002 to 1:1:0.20. The atom ratio of vanadium to phosphorus in the starting material is important since it controls the vanadium to phosphorus atom ratio in the final catalyst. When the oxidation catalysts herein contain a vanadium-phosphorus atom ratio below 0.10:1.00 or above 1.00, the yield of maleic anhydride using these catalysts is so low as to render the reaction commercially unattractive. It should be noted that phosphorus aids in stabilizing vanadium in the final catalyst composition, while tin +2 acts as a reducing agent which aids in the reduction of vanadium to a valency state of less than +5. It should additionally be noted that the above-described acids which dissolve the vanadium, phosphorus and tin compounds act as reducing agents for the vanadium compounds. However, the reduction process takes from one-half hour to about one hour when tin is not present in the reaction medium. Upon the addition of tin to the reaction medium, the reduction of vanadium to a valency of less than +5 takes place almost instantly, i.e., less than one minute. Generally, the vanadium is reduced to an average valence within the range of from +3.50 to +4.95, preferably from +4.10 to +4.70.

Conventional apparatus and techniques known to the art may be used to dissolve and react the components which make up the catalyst precursor. For example, temperatures of from 100° F. to 220° F., especially from 180° F. to 220° F. and a reaction time of from ½ hour to 6 hours under atmospheric pressure normally are sufficient to dissolve and react the vanadium, phosphorus and tin compounds. However, pressures from atmospheric pressure to 50 p.s.i.g. may be used to shorten the dissolution and reaction times. Generally, agitation is supplied during the reaction period to ensure complete contact of the reactants. Agitation is defined herein as mixing, rocking, shaking, etc.

After the reaction proceeds to completion the catalyst precursor is concentrated and collected using conventional methods and techniques and mixed with a zeolite of the mordenite crystal structure to form an impregnated mordenite.

The crystalline aluminosilicate employed in this invention is a zeolite of the mordenite crystal structure, which is highly siliceous in nature and is generally characterized by a silica-alumina mole ratio range of from about 6 to about 20 as found in nature. The mordenite crystal lattice comprises as the basic building block a tetrahedron consisting of one silicon or aluminum atom surrounded by four oxygen atoms. Each tetrahedron belongs to one or more four and five membered rings in the framework. The high degree of thermal stability of mordenite is probably due to the large number of five membered rings which are energetically favored in terms of stability.

Rings of twelve tetrahedral form pores or channels running parallel along the crystal axis of mordenite to give a tubular configuration. This structure is unique among the aluminosilicates or zeolites, because the channels or tubes do not intersect, and access to the cages or cavities is in one direction only. For this reason mordenite is referred to as two-dimensional. Other, well known zeolites, for example, faujasite, etc. contain twelve membered rings of tetrahedra, but they have interconnected cages which allow access from three directions.

Commercially available mordenites are typically prepared by heating an alkali metal aluminate in solution with an alkali metal hydroxide in contact with a silica source such as sodium silicate, reactive amorphous silica gel, or aqueous colloidal silica sol, at a temperature of about 180° to 220° F. Crystallization occurs over a relatively short period of time, for example, eight to twelve hours. The hydrogen form of mordenite is prepared by acid extraction of sodium mordenite with relatively strong mineral acids, for example hydrochloric acid, nitric acid, etc. Synthetic mordenite prepared in accordance with the above described procedure is available commercially from the Norton Company under the tradename of Zeolon. It should be noted that the hydrogen form of mordenite is preferred over the sodium form because the slightly acidic-hydrogen mordenite crystal structure enhances the formation of maleic anhydride using $C_4$ to $C_{10}$ hydrocarbons in an oxidation reaction.

The mordenite provides not only the required surface for the catalyst precursor, but gives physical strength and stability to the catalyst material. In addition, the mordenite has a large surface area upon which the catalyst precursor is deposited.

Generally, from 15 to 50 weight percent of the catalyst precursor comprising the oxides of vanadium, phosphorus and tin, is mixed with from 50 to 85 weight percent of the mordenite. Binding agents and additives may optionally be added to the catalyst to provide the proper consistency of the catalyst prior to mixing and forming said catalyst. The binding agents and additives, when used, preferably comprise from 0 to 10, especially from 3 to 10 weight percent of the finished catalyst. Suitable binding agents include methyl cellulose, silica, and alumina. Additives suitable for use herein include organic polar solvents such as ethanol, propanol, isopropanol, butanol, etc. The binding agents and additives are normally mixed in a weight ratio of from 1:20 to 20:1. The preferred method of mixing the catalyst precursor and mordenite is by comulling. However, other conventional mixing techniques may be used.

The physical form of the catalysts of this invention depends to a large extent upon the technique of drying and/or the desired shape. The catalysts may be produced as spheres, pellets, beads, elongated cylinders, and three-lobe or cloverleaf configurations. For example, the composites may be filtered and oven dried and course granules may be obtained by breaking up and sieving the oven-dried cake up to any desired size. Spray drying the catalyst, such that, the dried catalyst will pass through a 4 to 200 mesh sieve (U.S.) in another method of producing the desired catalyst. Another method involves shapeboring the catalyst into a desired configuration using a restraint to maintain the desired shape and thereafter drying the catalyst. A particularly desirable shape is a cylindrical configuration having a diameter of from 1/16 inch to ⅛ and a length of from ¼ inch to ½ inch.

The final catalyst is activated by calcination which preferably is performed in an air or oxygen atmosphere at a temperature of from about 400° F. to about 1,200° F., for about ¼ hour to about 6 hours, especially from about ½ hour to about 4 hours.

The catalyst thus produced is especially suited for oxidizing $C_4$ to $C_{10}$ hydrocarbons to maleic anhydride, and has a surface area of from 100 $M^2$/g to 450 $M^2$/g, a pore volume of from 0.1 cc/g to 0.8 cc/g and a compacted bulk density of from 0.5 to 1.5.

The above described catalysts of the present invention are useful for producing maleic anhydride from $C_4$ to $C_{10}$ hydrocarbons. A variety of reactors may be used in the oxidation reactions herein. For example, conventional fluidized bed reactors and fixed-bed or tube, heat exchanger type reactors are satisfactory, the details of the operation of such reactors are well known to those skilled in the art. The oxidation reaction is an exothermic reaction; thus, necessitating relatively close control of the reaction temperature. It is desirable to have the surface of the reactor at a constant temperature and some medium may be necessary to conduct heat away from the reactor to aid temperature control. Examples of desirable medium include molten sulfur, mercury, molten lead, or eutectic salt baths, for example a sodium nitrate-sodium nitrite-potassium nitrate eutectic constant temperature mixture. An additional method of temperature control is to use a metal block reactor whereby the metal surrounding the reactor chamber acts as a temperature regulating body or by conventional heat exchangers.

Normally a reaction mixture of a gaseous feed stream comprising a molecular oxygen containing gas, for example, air, a mixture of air and oxygen, mixtures of carbon dioxide and oxygen or mixtures of nitrogen or steam with air or oxygen, and a $C_4$ to $C_{10}$ hydrocarbon is charged to a reaction zone, for example, a conventional pressure reactor. The gaseous feed stream generally will contain a molecular oxygen containing gas and from about 0.1 to about 2.5 mole percent, especially from about 0.1 to about 1.5 mole percent of a $C_4$ to $C_{10}$ hydrocarbon for optimum yield of maleic anhydride. Although higher concentrations of hydrocarbon may be employed, they are not recommended because explosive hazards may be encountered.

The $C_4$ to $C_{10}$ hydrocarbons which are suitable for use are selected from straight and branched chain, and cyclic alkanes or olefins. Suitable $C_4$ to $C_{10}$ alkanes include butane, pentane, isopentane, cyclopentane, hexane, cyclohexane, heptane, cycloheptane, octane, nonane or decane or mixtures thereof. Olefins which may be used to produce maleic anhydride are selected from mono and di olefins containing 4 to 10 carbon atoms. For example, desirable olefins include butene, butadiene, pentene, cyclopentene, hexene, cyclohexene, heptene, cycloheptene, octene, nonene or decene or mixtures thereof.

Preferably the gaseous feed stream comprising a gas containing molecular oxygen and a $C_4$ to $C_{10}$ hydrocarbon are reacted in the presence of an oxidation catalyst described by the formula:

$$V_aP_bSn_cO_dX$$

wherein X is mordenite, a is 0.1 to 1, b is 1, c is 0.001 to 0.30 and d is a number which satisfies the valence requirements of the other elements present. The flow rate of the gaseous feed stream through the pressure reactor may be varied within rather wide limits but a preferred flow rate consists of a gas hourly space velocity (GHSV) of from 700 to 5,000 reciprocal hours.

The temperatures of reaction may be varied within some limits, but normally the reaction should be conducted at temperatures within a rather critical range. The overall temperature range for the $C_4$ to $C_{10}$ hydrocarbons preferably is from 500° F. to 1,200° F., especially from 600° F. to 1,000° F. It should be noted that the optimum oxidation temperatures for the alkanes and olefins differ. For example, the optimum oxidation temperature range for the $C_4$ to $C_{10}$ alkanes is from 750° F. to 1,200° F., preferably from 800° F. to 1,000° F. While the optimum oxidation temperature range for the olefins herein is from 500° F. to 900° F., especially from 600° F. to 900° F.

Typically, the reaction pressure is from atmospheric pressure to 200 p.s.i.g., preferably from atmospheric pressure to 50 p.s.i.g., as previously stated, the reaction may be carried out in any reactor suitable for effecting vapor-phase oxidation reactions, but preferably a fixed catalyst bed is employed.

The invention is further illustrated by the following examples which are illustrative of various aspects of the invention and are not intended as limiting the scope of the invention as defined by the appended claims.

EXAMPLE I

An oxidation catalyst is prepared by charging 28.0 grams of ammonium metavanadate and 100 ml of water to a 500 cc round bottom flask equipped with a water cooled condensor, heating mantel and magnetic stirrer. The above mixture is heated to a temperature of 130° F. and agitated with the magnetic stirrer for 3 minutes.

Next, 20 ml of concentrated hydrochloric acid, 3.6 grams of stannous chloride, 20 ml of ethyl alcohol and 60.4 grams of 85 percent phosphoric acid are added to the above mixture. The non-homogeneous solution, thus formed, exhibits a green color. Finally, the solution is refluxed for 16 hours, however, a shorter reflux time period may be used, for example, ½ hour or more.

The dark green slurry produced above (150 ml) and 240 grams of H+ mordenite are co-mulled with 20 grams of amorphous silica and 4 grams of methyl cellulose to achieve the proper consistency, using a model no. 472 Lancaster Mixer, manufactured commercially by the Posy Iron Works, Inc., Lancaster, Pa. The Mixer is operated at a speed of 36 RPM. The resulting slurry is extruded into cylindrical extrudates having an average length of ½ inch and an average diameter of 1/16 inch. The catalyst is activated by calcination at 932° F. in air for 3 hours and has a vanadium-phosphorus-tin atomic ratio of 0.43:1:034. The catalyst has a surface area of 308 M²/g and the vanadium has an average oxidation state of 4.37.

EXAMPLE II

Maleic anhydride is produced from n-butane by charging 25 ml of the catalyst of Example I to a reactor containing 82 ml of 4 to 6 mesh quartz granules. An additional 45 ml of 4 to 6 mesh quartz granules are added to the top of the catalyst as a preheat zone and n-butane distribution area. The reactor is a downflow tubular reactor having a length of 25 inches, an outside diameter of 1 inch, and an inside diameter of ¾ inch. In addition, the reactor is equipped with a ⅛ inch outside diameter, central-longitudinal thermowell. Air is charged to the reactor at the rate of 2.1 Standard Cubic Feet (SCF)/hour and n-butane is charged to the reactor at a rate of 0.03 SCF/hour. The Gas Hourly Space Velocity (GHSV) is 2,400 hours⁻¹ and the catalyst bed temperature is 977° F. at atmospheric pressure. Analysis indicates that 16.6 percent of the n-butane is converted to maleic anhydride, with a selectivity of 125 weight percent and a yield of 23.1 weight percent to maleic anhydride production.

EXAMPLE III

The procedure of Example II is used to produce maleic anhydride with the following exceptions:

Pentane is substituted for the butane, the reaction temperature is 919° F. and the feed stream comprises air containing 1.47 mole percent pentane. Substantially, the same conversion, selectivity and yield of maleic anhydride are obtained when pentane is substituted for butane.

EXAMPLES IV AND V

Maleic anhydride is produced from butene by charging 25 ml of the catalyst of Example I to a reactor containing 82 ml of 4 to 6 mesh quartz granules. An additional 45 ml of 4 to 6 mesh quartz granules are added to the top of the catalyst as a preheat zone and butene distribution area. The reactor is a downflow tubular reactor having a length of 25 inches, an outside diameter of 1 inch, and an inside diameter of ¾ inch. In addition, the reactor is equipped with a ⅛ inch outside diameter, central-longitudinal thermowell. A feed stream comprising air containing 1.5 mole percent of butene is charged to the reactor at the rate of 2.1 Standard Cubic Feet (SCF)/hour. The reaction is conducted at atmospheric pressure. In addition, the temperature and gas hourly space velocity (GHSV) are varied in accordance with Table 1 below.

TABLE 1

| Ex | GHSV (Hours⁻¹) | T (°F.) | Weight Percent Conversion | Weight Percent Selectivity | Weight Percent Yield |
|---|---|---|---|---|---|
| IV | 2,500 | 766 | 78.9 | 66.8 | 52.5 |
| V | 5,000 | 775 | 39.9 | 77.2 | 30.8 |

Obviously, many modifications and variations of this invention, as hereinbefore set forth, may be made without departing from the spirit and scope thereof, and therefore only such limitations should be imposed as are indicated in the appended claims.

I claim:

1. An oxidation catalyst described by the formula:

$$V_aP_bSn_cO_dX$$

wherein X is mordenite, a is 0.10 to 1, b is 1, c is 0.001 to 0.30, and d is a number which satisfies the valence requirements of the other elements present.

2. The oxidation catalyst defined in claim 1 wherein X is hydrogen mordenite.

3. The oxidation catalyst defined in claim 1 wherein the vanadium has an average valence between +3.50 and +4.95.

4. The oxidation catalyst defined in claim 1 wherein the vanadium has an average valence between +4.10 and +4.70.

5. The oxidation catalyst defined in claim 1 wherein the vanadium:phosphorus:tin atomic ratio is from 0.20:1:0.002 to 1:1:0.20.

6. The oxidation catalyst defined in claim 1 wherein from 15 to 50 weight percent of V, P, Sn and O as the metal oxides is combined with from 50 to 85 weight percent of X.

7. The oxidation catalyst defined in claim 1 optionally containing from 0 to 10 weight percent of a binder selected from the group consisting of silica, methyl cellulose and alumina, and mixtures thereof.

8. The oxidation catalyst defined in claim 1 having a surface area of from 100 M²/g to 450 M²/g, a pore volume of from 0.1 cc/g to 0.8 cc/g, and a compacted bulk density of from 0.50 to 1.50 g/cc.

9. An oxidation catalyst described by the formula:

$$V_aP_bSn_cO_dX$$

wherein X is hydrogen mordenite, a is 0.10 to 1, b is 1, c is 0.001 to 0.30, and d is a number which satisfies the valence requirements of the other elements present, vanadium has an average valence between +3.50 and +4.95, wherein said oxidation catalyst contains from 15 to 50 weight percent of V, P, Sn and O as the metal oxides, from 50 to 85 weight percent of X, and from 0 to 10 weight percent of a binder selected from the group consisting of silica, methyl cellulose and alumina and mixtures thereof, said oxidation catalyst having a surface area of from 100 M²/g to 450 M²/g, a pore volume of from 0.1 cc/g to 0.8 cc/g, and a compacted bulk density of from 0.50 to 1.50 g/cc.

10. A method of preparing a vanadium, phosphorus, tin, oxygen and mordenite, oxidation catalyst which comprises:

(A) contacting a vanadium compound and a phosphorus compound with an acidic-aqueous medium and a divalent tin compound under reaction conditions which will produce vanadium having an average valence of from +3.50 to +4.95, to form a catalyst precursor;

(B) mixing the catalyst precursor with mordenite, to form an impregnated mordenite; and (C) calcining the oxidation catalyst at temperatures in the range of from 400° F. to 1,200° F., for from ¼ hour to 6 hours.

11. The method defined in claim 10 wherein the oxidation catalyst contains vanadium, phosphorus and tin in an atomic ratio of from 0.20:1:0.002 to 1:1:0.20.

12. The method defined in claim 10 wherein from 15 to 50 weight percent of the catalyst precursor is mixed with from 50 to 85 weight percent of mordenite.

13. The method defined in claim 10 wherein the vanadium compound is a member selected from the group consisting of ammonium vanadate, vanadyl sulfate, vanadium pentoxide and vanadium oxytrichloride, and mixtures thereof.

14. The method defined in claim 10 wherein the phosphorus compound is a member selected from the group consisting of phosphoric acid, phosphorus pentoxide, ammonium phosphate and diammonium phosphate, and mixtures thereof.

15. The method defined in claim 10 wherein the tin compound is stannous chloride, stannous fluoride, stannous bromide, stannous oxide, stannous sulfate, stannous acetate, stannous pyrophosphate, or stannous oxalate, or a mixture thereof.

16. The method defined in claim 10 wherein the acidic-aqueous medium comprises water and an acid selected from the group consisting of hydrochloric acid, hydroiodic acid, hydroformic acid, acetic acid, oxalic acid, maleic acid, citric acid or formic acid, or a mixture thereof.

17. The method defined in claim 10 comprising mixing from 0 to 10 weight percent of a binding agent and solvent in a weight ratio of from 1:20 to 20:1, with the catalyst precursor and mordenite in step (B).

18. The method defined in claim 17 wherein the binding agent is a member selected from the group consisting of silica, methyl cellulose and alumina, and mixtures thereof.

19. The method defined in claim 17 wherein the solvent is a member selected from the group consisting of ethanol, propanol, isopropanol, and butanol, and mixtures thereof.

20. The method defined in claim 10 wherein the reaction conditions comprise temperatures from 100° F. to 220° F. and pressures from atmospheric pressure to 50 p.s.i.g.

21. The method defined in claim 10 wherein the oxidation catalyst has a surface area of from 100 $M^2/g$ to 450 $M^2/g$, a pore volume of from 0.1 cc/g to 0.8 cc/g, and a compacted bulk density of from 0.50 to 1.50 g/cc.

22. A method of preparing a vanadium, phosphorus, tin, oxygen and mordenite oxidation catalyst which comprises:

(A) contacting a pentavalent vanadium compound, a pentavalent phosphorus compound and a divalent tin compound, at an atomic ratio of from 0.10:1:0.001 to 1:1:0.30 with an acidic-aqueous medium at a temperature of from 100° F. to 220° F., and a pressure from atmospheric pressure to 50 p.s.i.g., to form a catalyst precursor and produce vanadium having an average valence of from +3.50 to +4.95;

(B) mixing from 15 weight percent to 50 weight percent of said catalyst precursor with from 50 weight percent to 85 weight percent of mordenite to form an impregnated mordenite; and (C) calcining the oxidation catalyst at temperatures in the range of from 400° F. to 1,200° F., for ½ hour to 6 hours.

23. The method defined in claim 22 wherein the vanadium compound is a member selected from the group consisting of ammonium vanadate, vanadyl sulfate, vanadium pentoxide, and vanadium oxytrichloride, and mixtures thereof.

24. The method defined in claim 22 wherein the phosphorus compound is a member selected from the group consisting of phosphoric acid, phosphorus pentoxide, ammonium phosphate, and diammonium phosphate, and mixtures thereof.

25. The method defined in claim 22 wherein the tin compound is stannous chloride, stannous fluoride, stannous bromide, stannous oxide, stannous sulfate, stannous acetate, stannous pyrophosphate, or stannous oxalate, or a mixture thereof.

26. The method defined in claim 22 wherein the acidic-aqueous medium consists of water and an acid selected from the group consisting of hydrochloric acid, hydroiodic acid, hydroformic acid, acetic acid, oxalic acid, maleic acid, citric acid or formic acid, or a mixture thereof.

27. The method defined in claim 22 wherein from 0 to 10 weight percent of a binding agent and solvent in a weight ratio of from 1:20 to 20:1 is mixed with the catalyst precursor and mordenite in step (B).

28. The method defined in claim 27 wherein the binding agent is selected from the group consisting of silica, methyl cellulose and alumina.

29. The method defined in claim 27 wherein the solvent is a member selected from the group consisting of ethanol, propanol, isopropanol, and butanol, and mixtures thereof.

30. The method defined in claim 22 wherein the oxidation catalyst has a surface area of from 100 $M^2/g$ to 450 $M^2/g$, a pore volume of from 0.10 cc/g to 0.80 cc/g, and a compacted bulk density of 0.50 to 1.50 g/cc.

31. A method of preparing a vanadium, phosphorus, tin, oxygen and mordenite, oxidation catalyst having a surface area of from 100 $M^2/g$ to 450 $M^2/g$, a pore volume of from 0.10 cc/g to 0.80 cc/g, and a compacted bulk density of from 0.50 to 1.50, which comprises:

(A) Contacting ammonium metavanadate, phosphoric acid and stannous chloride at an atomic ratio of from 0.10:1:0.001 to 1:1:0.30 with aqueous hydrochloric acid at a temperature of from 100° F. to 220° F., and a pressure of from atmospheric pressure to 50 p.s.i.g., to form a catalyst precursor, wherein the vanadium has an average valence of from +3.50 to +4.95;

(B) mixing from 15 weight percent to 50 weight percent of said catalyst precursor and from 50 weight percent to 85 weight percent of mordenite with from about 0 to 10 weight percent of a binding agent selected from the group consisting of silica, methyl cellulose and alumina and mixtures thereof, and a solvent selected from the group consisting of ethanol, propanol, isopropanol, and butanol and mixtures thereof in a binding agent and solvent weight ratio of from 1:20 to 20:1 to form an impregnated mordenite; and (C) calcining the oxidation catalyst at a temperature in the range of from 400° F. to 1,200° F., for ½ hour to 6 hours.

* * * * *